United States Patent
Wang

(10) Patent No.: US 10,772,820 B2
(45) Date of Patent: Sep. 15, 2020

(54) COMPOSITION FOR CLEANSING A KERATIN MATERIAL CONTAINING AN AMINO ACID SURFACTANT

(71) Applicant: L'OREAL, Paris (FR)

(72) Inventor: Huifeng Wang, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/571,398

(22) PCT Filed: Jul. 22, 2015

(86) PCT No.: PCT/CN2015/084763
§ 371 (c)(1),
(2) Date: Nov. 2, 2017

(87) PCT Pub. No.: WO2017/012087
PCT Pub. Date: Jan. 26, 2017

(65) Prior Publication Data
US 2018/0116941 A1    May 3, 2018

(51) Int. Cl.
| | |
|---|---|
| *C11D 1/10* | (2006.01) |
| *C11D 1/12* | (2006.01) |
| *C11D 3/22* | (2006.01) |
| *C11D 3/26* | (2006.01) |
| *A61K 8/73* | (2006.01) |
| *A61K 8/44* | (2006.01) |
| *A61Q 19/10* | (2006.01) |
| *C11D 1/04* | (2006.01) |
| *A61Q 19/04* | (2006.01) |

(52) U.S. Cl.
CPC ............... *A61K 8/733* (2013.01); *A61K 8/44* (2013.01); *A61Q 19/04* (2013.01); *A61Q 19/10* (2013.01); *C11D 1/04* (2013.01); *C11D 1/10* (2013.01); *C11D 1/12* (2013.01); *C11D 3/22* (2013.01); *C11D 3/222* (2013.01)

(58) Field of Classification Search
CPC .... C11D 1/04; C11D 1/10; C11D 1/12; C11D 3/22; C11D 3/222
USPC .......... 510/124, 125, 36, 137, 338, 470, 473
See application file for complete search history.

(56) References Cited

U.S. PATENT DOCUMENTS

| | | | |
|---|---|---|---|
| 5,712,232 A | 1/1998 | Moriyama et al. | |
| 8,673,879 B2 | 3/2014 | Thoerner et al. | |
| 8,778,864 B2* | 7/2014 | Andjelic | A61K 8/39 510/467 |
| 2004/0186037 A1* | 9/2004 | Cheung | A01N 59/14 510/426 |
| 2005/0020471 A1* | 1/2005 | Cheung | C11D 3/042 510/463 |
| 2006/0079415 A1* | 4/2006 | Kozubal | A61K 8/24 510/119 |
| 2006/0194709 A1* | 8/2006 | Boone | C11D 1/83 510/383 |
| 2010/0285077 A1* | 11/2010 | Lintner | A61K 8/46 424/401 |
| 2011/0305648 A1* | 12/2011 | Knapek | A61K 8/42 424/56 |
| 2013/0040869 A1* | 2/2013 | Cox | A61K 8/44 510/119 |

FOREIGN PATENT DOCUMENTS

| | | |
|---|---|---|
| JP | 2003-95867 A | 4/2003 |
| WO | 2011/012394 A1 | 2/2011 |
| WO | 2011/130460 A1 | 10/2011 |

OTHER PUBLICATIONS

International Search Report and Written Opinion dated Apr. 28, 2016, in PCT/CN2015/084763, filed Jul. 22, 2015.

* cited by examiner

*Primary Examiner* — Gregory R Delcotto
(74) *Attorney, Agent, or Firm* — Oblon, McClelland, Maier & Neustadt, L.L.P.

(57) ABSTRACT

Disclosed is a composition for cleansing a keratin material, comprising, in an aqueous phase: a) at least one amino acid surfactant; b) calcium alginate, wherein the weight ration (a/b) of a) amino acid surfactant and b) calcium alginate is from 0.7 to 6.

16 Claims, No Drawings

COMPOSITION FOR CLEANSING A KERATIN MATERIAL CONTAINING AN AMINO ACID SURFACTANT

The present invention relates to a composition for cleansing a keratin material containing an amino acid surfactant.

Cleansing the skin is very important especially for caring for the face. It must be as efficient as possible because greasy residues, such as dirt, excess sebum, the remnants of cosmetic products used daily, and make-up products can result in an unpleasant oily appearance. Several types of skin cleansing products, for example, rinsable cleansing anhydrous oils and gels, foaming creams, lotions and gels, and non-foaming compositions are known.

Rinsable anhydrous oils and gels have a cleansing action and are able to disperse make-up pigments. These products are effective and well tolerated. However, they exhibit the disadvantage of being heavy, and of not conferring a feeling of freshness on application, which is disadvantageous from a cosmetic viewpoint.

Cleansing products of emulsion type also exist on the market, by using various emulsifiers with cleansing properties, in combination with skin conditioning agents.

Nowadays it has become more and more important that cleansing compositions provide effective cleansing of the keratin material as well as mildness for said keratin material. Additional attempts to attenuate the adverse irritant effects of anionic surfactants have been made by replacing some of the foam generating anionic surfactant with very mild secondary surfactants. The anionic surfactant is utilized in conjunction with a nonionic and/or an amphoteric surfactant as disclosed in U.S. Pat. No. 4,726,915. However, reducing the amount of anionic surfactant in a cleansing or cleaning composition adversely affects the detersive properties of the composition.

As a result, mild surfactants, such as amino acid surfactants, are being used more frequently to meet consumer requirements for a mild, high satisfactory cleanser. Amino acid based surfactants are known for their mildness towards the skin and eyes, conditioning benefits to hair and skin, foam generating properties, and the ability to maintain a stable foam profile in the presence of sebum. Moreover, these surfactants are environmentally friendly in that they are derived from naturally occurring renewable resources such as vegetable oils and amino acids. However, compared to ethoxylated alkyl sulfate surfactants, amino acid based surfactants are not easy to formulate because they are hard to thicken when formulated with the commonly available rheology modifiers or thickeners on the market. Ideal viscosity should be achieved while maintaining the ability to provide good cleansing properties. The ideal viscosity allows for the controlled handling and dispensing of the product during use as compared to a thinner product. In personal care cleansing applications, thick compositions are needed. An ideal viscosity profile permits the formulation of an easy to use product that does not run-off when applied to non-horizontal body surfaces, such as face. The shear thinning profile of the liquid body cleansing composition should exhibit a higher viscosity at low shear conditions and lower viscosity at high shear conditions to aid in the application and removal of the product from the body. These properties are especially useful if the cleansing compositions are to be topically applied to human skin and hair. Many rheology modifiers are known. Compositions comprising amino acid surfactants are for example described in WO 2011/130460. WO 2011/130460 teaches using synthetic hydrophobically modified polymers to thicken amino acid containing compositions, but discourages using natural rheology modifiers, because they provide poor flow and leveling properties.

However the composition as such is still not satisfying. None of the prior arts mentioned above had disclosed a composition for cleansing a keratin material with a desired fast rinse off speed. However, obtaining simultaneously a fast rinse-off and the desired viscosity is not easy in the art of cleansing compositions.

Besides, there is a need for a composition for cleansing a keratin material, comprising a good cleansing ability and a mildness feeling after application.

DISCLOSURE OF INVENTION

An objective of the present invention is to provide a composition for cleansing a keratin material, overcoming the above technical problems.

The invention aims to provide good viscosity for a composition for cleansing a keratin material, in particular for cleansing the skin.

The invention aims to provide a composition for cleansing a keratin material, providing good skin feeling, and in particular a composition which is mild for a keratin material.

By "skin feeling" it means softness, smoothness, mild without feeling of dry or sticky.

The invention aims to provide a composition for cleansing a keratin material, in particular skin, providing good rinse-off speed.

More particularly, the invention also aims to provide a composition for cleansing a keratin material, with good viscosity and which is mild for a keratin material, especially skin, and more particularly face skin.

More particularly, the invention also aims to provide a composition for cleansing a keratin material with good viscosity and good rinse-off speed.

"Rinse-off speed" means the quickness the strongest squeaky feeling of whole face occurs. Rinse-off speed is evaluated tactilely during several rinsing movements, when fingers "rub" face from top to bottom of cheeks in accordance with rotational movement. A good "rinse-off speed" means a low number of rounds according to this evaluation.

Preferably, the invention aims to provide a composition for cleansing a keratin material, with good viscosity, good rinse-off speed and which is mild for a keratin material, especially skin, and more particularly face skin.

The invention also aims to provide such compositions with good stability upon storage.

The present invention also relates to a process for cleansing the skin, in particular the face, wherein the composition according to the present invention is applied to the skin, in particular to the face.

The above technical problems have been solved by the present invention.

BEST MODE FOR CARRYING OUT THE INVENTION

The inventors performed research, and have unexpectedly found that a combination of calcium alginate and at least one amino acid surfactant can provide a composition for cleansing a keratin material, overcoming one or more of the above technical problems.

As used herein, the term "keratin material(s)" is understood to mean the skin, the nails, or the mucous membranes, and, in at least one embodiment, refers to the skin.

Preferably, the keratin material according to the present invention is the skin. By "skin", it is intended all the body skin. Still preferably, the keratin material is the skin of the face.

Another subject of the present invention is a cosmetic method for cleansing a keratin material, preferably the skin, more preferably the face, comprising a step of applying the composition as defined above to said keratin material.

Another aspect of the present invention is a use of the composition for cleansing a keratin material, preferably the skin, more preferably the face.

In one embodiment, the present invention relates to foaming compositions. A foaming composition is a composition generating foam after the composition is deposited on keratin materials and upon friction of the keratin materials with an effective quantity of water. The foaming properties of a composition may be determined by its volume of foam. The higher volume, the better foaming property is.

In one embodiment, the present invention relates to non-foaming compositions. Non-foaming composition does not generate foam, for example as measured by the method for evaluating the volume of foam.

Other features and advantages of the invention will emerge more clearly from the reading of the description and examples which follow.

In what follows, the expression "at least one" is equivalent to "one or more" and, unless otherwise indicated, the limits of a range of values are included in that range.

Thus, the composition according to the present invention is a composition for cleansing a keratin material, comprising, in an aqueous phase:
a) at least one amino acid surfactant;
b) calcium alginate,
wherein the weight ratio (a/b) of a) amino acid surfactant and b) calcium alginate is from 0.7 to 6.

Accordingly, the composition of the present invention comprises calcium alginate.

Alginic acid is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks) or alternating M and G-residues (MG-blocks).

Alginates are refined from brown seaweeds. A wide variety of brown seaweeds of the phylum Phaeophyceae are harvested throughout the world to be converted into the raw material commonly known as sodium alginate. Calcium alginate is a water-insoluble, gelatinous, cream coloured substance that can be obtained through the addition of aqueous calcium chloride to aqueous sodium alginate.

Calcium alginate is marketed for example by Qingdao Bright Moon Seaweed Group Co. Ltd.

The amount of calcium alginate ranges from 0.5 weight percent to 10 weight percent, preferably from 1 weight percent to 6 weight percent, based on the total weight of the composition. The composition also comprises at least one amino acid surfactant.

In one embodiment, said amino acid surfactant is derived from a carboxylate salt of amino acid wherein the amine group situated on the α-carbon or β-carbon of an amino acid salt is acylated with a $C_8$ to $C_{22}$ fatty acid derivative.

The carboxylate salts of these amino acids can be formed by conventional means such as by neutralization of the respective amino acid with a base. The amine group situated on the α-carbon or β-carbon of the neutralized amino acid is acylated with a fatty acid halide (acyl halide) in the presence of a base via the well-known Schotten-Baumann reaction giving the amide, thus forming the desired surfactant reaction product, i.e. the amino acid surfactant. Suitable acyl halides for acylation of the amino acid carboxylate salt include acyl chlorides, bromides, fluorides, and iodides. The acyl halides can be prepared by reacting a saturated or unsaturated, linear or branched $C_8$ to $C_{22}$ fatty acid with a thionyl halide (bromide, chloride, fluoride, and iodide). Representative acyl halides include but are not limited to the acyl chlorides selected from decanoyl chloride, dodecanoyl chloride (lauroyl chloride), cocoyl chloride (coconut oil derived fatty acid chlorides) tetradecanoyl chloride (myristoyl chloride), hexadecanoyl chloride (palmitoyl chloride), octadecanoyl chloride (stearoyl chloride), 9-octadecenoyl chloride (oleoyl chloride), eicosanoyl chloride (arachidoyl chloride), docosanoyl chloride (behenoyl chloride), and any mixture thereof. Other acyl halides include the bromides, fluorides and iodides of the foregoing fatty acids. A method for preparing acyl halides as well as an alternative method for acylating amino acids is set forth in US Patent Application Publication No. 2008/0200704, published on Aug. 21, 2008, which application is incorporated herein by reference.

In one embodiment, said amino acid surfactant is represented by the formula (I):

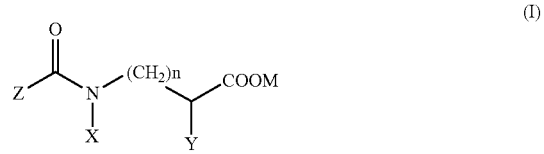

wherein:
Z represents a saturated or unsaturated, linear or branched hydrocarbon group having 8 to 22 carbon atoms,
X is hydrogen or methyl group,
n is 0 or 1,
Y is selected from hydrogen, $-CH_3$, $-CH(CH_3)_2$, $-CH_2CH(CH_3)_2$, $-CH(CH_3)CH_2CH_3$, $-CH_2C_6H_5$, $-CH_2C_2H_4OH$, $-CH_2OH$, $-CH(OH)CH_3$, $-(CH_2)_4NH_2$, $-(CH_2)_3NHC(NH)NH_2$, $-CH_2C(O)O^-M^+$, $-(CH_2)_2C(O)OH$, $-(CH_2)_2C(O)O^-M^+$, and
M is a salt-forming cation wherein COO is the counter-anion, such as for example sodium, potassium, ammonium, or triethanolamine.

Thus according to the present invention, the amino acid surfactant is represented by the formula (I),

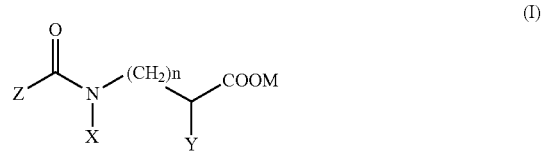

wherein:
Z represents a saturated or unsaturated, linear or branched hydrocarbon group having 8 to 22 carbon atoms,
X is hydrogen or methyl group,
n is 0 or 1,
Y is selected from hydrogen, $-CH_3$, $-CH(CH_3)_2$, $-CH_2CH(CH_3)_2$, $-CH(CH_3)CH_2CH_3$, $-CH_2C_6H_5$, $-CH_2C_2H_4OH$, $-CH_2OH$, $-CH(OH)CH_3$, $-(CH_2)_4$ NH$_2$, —(CH$_2$)$_3$NHC(NH)NH$_2$, —CH$_2$C(O)O$^-$M$^+$, —(CH$_2$)$_2$ C(O)OH, —(CH$_2$)$_2$C(O)O$^-$M$^+$, and M is a salt-forming cation wherein COO is the counter-anion, such as for example sodium, potassium, ammonium, or triethanolamine.

In one embodiment, in formula (I):
Z represents a saturated or unsaturated, linear or branched C$_8$ to C$_{22}$ alkyl group,
X is a hydrogen or methyl group,
n is 0,
Y is selected from hydrogen, —(CH$_2$)$_2$C(O)OH, —(CH$_2$)$_2$C(O)O$^-$M$^+$, and
M is a salt-forming cation wherein COO is the counter-anion, such as for example sodium, potassium, ammonium, or triethanolamine.

According to a preferred embodiment of the invention, in the amino fatty acid of formula (I):
Z represents a saturated or unsaturated, linear or branched C$_8$ to C$_{22}$ alkyl group,
X is a hydrogen or methyl group,
n is 0,
Y is selected from hydrogen, —(CH$_2$)$_2$C(O)OH, —(CH$_2$)$_2$C(O)O$^-$M$^+$, and
M is a salt-forming cation wherein COO is the counter-anion, such as for example sodium, potassium, ammonium, or triethanolamine.

Examples of the amino acid surfactants are salt of alanine, arginine, aspartic acid, glutamic acid, glycine, isoleucine, leucine, lysine, phenylalanine, serine, tyrosine, valine, sarcosine, and any mixture thereof. More specifically, mentions can be made of the amino acid surfactants such as dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alaninate, lauroyl β-alaninate, lauroyl methyl β-alaninate, myristoyl β-alaninate, potassium lauroyl methyl β-alaninate, sodium cocoyl alaninate, sodium cocoyl methyl β-alaninate and sodium myristoyl methyl β-alaninate palmitoyl glycinate, sodium lauroyl glycinate, sodium cocoyl glycinate, sodium myristoyl glycinate, potassium lauroyl glycinate, potassium cocoyl glycinate, potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate ammonium lauroyl sarcosinate, sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate, and mixtures thereof.

References can be made to the commercially available amino acid surfactant of, for example, acylsarcosinates, for instance the sodium lauroyl sarcosinate sold under the name Sarkosyl NL 97® by the company Ciba or sold under the name Oramix L 30® by the company SEPPIC, the sodium myristoyl sarcosinate sold under the name Nikkol Sarcosinate MN® by the company Nikkol or the sodium palmitoyl sarcosinate sold under the name Nikkol Sarcosinate PN® by the company Nikkol; alaninates, for instance the sodium N-lauroyl-N-methylamidopropionate sold under the name Sodium Nikkol Alaninate LN 30® by the company Nikkol or sold under the name Alanone ALE® by the company Kawaken, and the N-lauroyl-N-methylalanine triethanolamine sold under the name Alanone Alta® by the company Kawaken; N-acylglutamates, for instance the triethanolamine monococoylglutamate sold under the name Acylglutamate CT-12® by the company Ajinomoto and the triethanolamine lauroylglutamate sold under the name Acylglutamate LT-12® by the company Ajinomoto; glycinates, for instance sodium N-cocoylglycinate sold under the name Amilite GCS-12® by the company Ajinomoto; aspartates, for instance the mixture of triethanolamine N-lauroyl aspartate and of triethanolamine N-myristoylaspartate, sold under the name Asparack® by the company Mitsubishi; citrates, and any mixture thereof.

According to the present invention, the preferred amino acid surfactant is selected from sodium lauroyl sarcosinate, sodium cocoyl glycinate, sodium cocoyl glutamate, disodium cocoyl glutamate, sodium lauroyl glutamate, or a mixture thereof.

Mentions of the preferred amino acid surfactant in the composition which is commercially available can be made to sodium lauroyl sarcosinate (ORAMIX L 30 sold by Seppic), sodium cocoyl glycinate (and) water (AMILITE® GCS-12K sold by Ajinomoto), sodium cocoyl glutamate (and) disodium cocoyl glutamate (AMISOFT® CS-22 sold by Ajinomoto), and sodium lauroyl glutamate (AMISOFT® LS-11 sold by Ajinomoto).

In one embodiment, the amount of amino acid surfactant ranges from 1 weight percent to 20 weight percent, preferably from 1.5 weight percent to 15 weight percent, more preferably from 2 weight percent to 10 weight percent, based on the total weight of the composition.

According to different embodiments, the composition of the present invention can be in form of foaming or non-foaming composition.

Accordingly, when the amino acid surfactant is used solely as the surfactant of the present invention, the composition is a non-foaming composition with a weight ratio of the amino acid surfactant being less than 4.5 weight percent, relative to the total weight of the composition.

According to another variation, when the amino acid surfactant is used solely as the surfactant of the present invention, the composition is a foaming composition with a weight ratio of the amino acid surfactant being from 4.5 to 20 weight percent, relative to the total weight of the composition.

This said, when additional surfactant is present in the composition of the present invention, the amount of the amino acid surfactant can be adjusted despite the above mentioned limitations, i.e., less than 4.5 weight percent for non-foaming composition and from 4.5 to 20 weight percent for foaming composition, in non-foaming or foaming compositions of the present invention.

According to the present invention, the ratio (a/b) of a) the amino acid surfactant and b) the calcium alginate of the composition ranges from 0.7 to 6. The weight ratio (a/b) of a) the amino acid surfactant and b) the calcium alginate enables the composition having ideal viscosities, i.e., allows for the controlled handling and dispensing of the composition of the present invention during use as compared to a thinner product. An ideal viscosity profile permits the composition of the invention an easy to use product that does not run-off when applied to non-horizontal body surfaces, such as face.

In one embodiment, the weight ratio (a/b) of a) the amino acid surfactant and b) the calcium alginate is from 0.75 to 5.

In one embodiment, the composition of the invention comprises:
from 0.5 weight percent to 10 weight percent, or from 1 weight percent to 6 weight percent, calcium alginate based on the total weight of the composition;
from 1 weight percent to 20 weight percent, or from 1.5 weight percent to 15 weight percent, or from 2 weight percent to 10 weight percent, amino acid surfactant(s) based on the total weight of the composition; and
water;
wherein the weight ratio (a/b) of a) the amino acid surfactant(s) and b) the calcium alginate is from 0.7 to 6.

In one preferred embodiment, the composition of the invention comprises:
from 0.5 weight percent to 10 weight percent, or from 1 weight percent to 6 weight percent, calcium alginate based on the total weight of the composition;
from 1 weight percent to 20 weight percent, or from 1.5 weight percent to 15 weight percent, or from 2 weight percent to 10 weight percent, amino acid surfactant(s) based on the total weight of the composition; and
water;
wherein the weight ratio (a/b) of a) the amino acid surfactant(s) and b) the calcium alginate is from 0.7 to 6, and wherein the amino acid surfactant is represented by the formula (I):

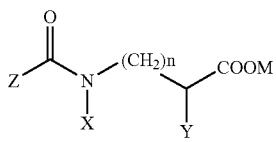

(I)

wherein:
Z represents a saturated or unsaturated, linear or branched hydrocarbon group having 8 to 22 carbon atoms,
X is hydrogen or methyl group,
n is 0 or 1,
Y is selected from hydrogen, —CH$_3$, —CH(CH$_3$)$_2$, —CH$_2$CH(CH$_3$)$_2$, —CH(CH$_3$)CH$_2$CH$_3$, —CH$_2$C$_6$H$_5$, —CH$_2$C$_2$H$_4$OH, —CH$_2$OH, —CH(OH)CH$_3$, —(CH$_2$)$_4$NH$_2$, —(CH$_2$)$_3$NHC(NH)NH$_2$, —CH$_2$C(O)O$^-$M$^+$, —(CH$_2$)$_2$ C(O)OH, —(CH$_2$)$_2$C(O)O$^-$M$^+$, and
M is a salt-forming cation wherein COO is the counter-anion, such as for example sodium, potassium, ammonium, or triethanolamine.

In one preferred embodiment, the composition of the invention comprises:
from 0.5 weight percent to 10 weight percent, or from 1 weight percent to 6 weight percent, calcium alginate based on the total weight of the composition;
from 1 weight percent to 20 weight percent, or from 1.5 weight percent to 15 weight percent, or from 2 weight percent to 10 weight percent, amino acid surfactant(s) based on the total weight of the composition; and
water;
wherein the weight ratio (a/b) of the a) amino acid surfactant(s) and b) the calcium alginate is from 0.7 to 6, and wherein the amino acid surfactant is selected from sodium lauroyl sarcosinate, sodium cocoyl glycinate, sodium cocoyl glutamate, disodium cocoyl glutamate, sodium lauroyl glutamate, or a mixture thereof.

According to an embodiment, the present invention relates to a method for cleansing a keratin material, especially the skin, comprising the application of a composition according to the invention.

Optionally, the method comprises a step of rinsing off the composition of the present invention by water.

Other Surfactant

The composition of the present invention may further comprise at least one additional surfactant, which is different from the amino acid surfactant as described above.

The additional surfactant can be selected from any types of surfactants conventionally known for composition for cleansing ketarin materials.

Preferably, the additional surfactant is selected from non-ionic surfactants.

More preferably, the composition of the present invention, when in form of foaming composition, further comprises at least one nonionic surfactant.

Even more preferably, when present, the amount of the nonionic surfactant is no greater than the amount of the amino acid surfactant a) as described above.

They may be chosen from alcohols, α-diols and (C$_{1-20}$) alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or alternatively these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—(C$_{6-24}$ alkyl)glucamine derivatives, amine oxides such as (C$_{10-14}$ alkyl)amine oxides or N—(C$_{10-14}$ acyl) aminopropylmorpholine oxides.

Mention may also be made of nonionic surfactants of alkyl(poly)glycoside type, represented especially by the following general formula:

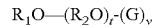

in which:
R$_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;
R$_2$ represents an alkylene radical comprising 2 to 4 carbon atoms,
G represents a sugar unit comprising 5 to 6 carbon atoms,
t denotes a value ranging from 0 to 10 and preferably 0 to 4,
v denotes a value ranging from 1 to 15 and preferably 1 to 4.

Preferably, the alkylpolyglycoside surfactants are compounds of the formula described above in which:

$R_1$ denotes a linear or branched, saturated or unsaturated alkyl radical comprising from 8 to 18 carbon atoms, $R_2$ represents an alkylene radical comprising 2 to 4 carbon atoms, t denotes a value ranging from 0 to 3 and preferably equal to 0, G denotes glucose, fructose or galactose, preferably glucose;

the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. $C_8/C_{16}$ alkyl(poly)glycosides 1,4, and especially decyl glucosides and caprylyl/capryl glucosides, are most particularly preferred.

Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

Preferably, use is made of $C_8/C_{16}$-alkyl(poly)glycosides 1,4, especially as an aqueous 53% solution, such as those sold by Cognis (BASF) under the reference Plantacare® 818 UP.

Preferentially, the nonionic surfactants are chosen from ($C_{6-24}$ alkyl)polyglycosides, and more particularly ($C_{8-18}$ alkyl)(poly)glycosides, ethoxylated $C_8$-$C_{30}$ fatty acid esters of sorbitan, polyethoxylated $C_8$-$C_{30}$ fatty alcohols and polyoxyethylenated $C_8$-$C_{30}$ fatty acid esters, these compounds preferably containing from 2 to 150 mol of ethylene oxide, and mixtures thereof.

Preferably, when they are present, the composition according to the invention comprises the said nonionic surfactant(s) in an amount ranging from 0.01 weight percent to 15 weight percent, preferably ranging from 0.1 weight percent to 10 weight percent, more preferably from 1 weight percent to 7 weight percent, based on the total weight of the composition.

According to a preferred embodiment, the composition of the present invention is in form of a foaming composition, comprising:

from 0.5 weight percent to 10 weight percent, preferably from 1 weight percent to 6 weight percent, calcium alginate based on the total weight of the composition;

from 4.5 weight percent to 20 weight percent of amino acid surfactant(s) based on the total weight of the composition;

from 0.01 weight percent to 15 weight percent, preferably from 0.1 weight percent to 10 weight percent, more preferably from 1 weight percent to 7 weight percent of nonionic surfactant(s) based on the total weight of the composition;

and water;

wherein the weight ratio of the amino acid surfactant(s) and the calcium alginate is from 0.7 to 6.

More preferably, the foaming composition comprises:
from 0.5 weight percent to 10 weight percent, preferably from 1 weight percent to 6 weight percent, calcium alginate based on the total weight of the composition;
from 4.5 weight percent to 20 weight percent amino acid surfactant(s) based on the total weight of the composition;
from 0.01 weight percent to 15 weight percent, preferably from 0.1 weight percent to 10 weight percent, preferably from 1 weight percent to 7 weight percent of nonionic surfactant(s) based on the total weight of the composition;
and
water;
wherein the weight ratio (a/b) of a) the amino acid surfactant(s) and b) the calcium alginate is from 0.7 to 6, the amino acid surfactant is selected from sodium lauroyl sarcosinate, sodium cocoyl glycinate, sodium cocoyl glutamate, disodium cocoyl glutamate, sodium lauroyl glutamate, or a mixture thereof; and the nonionic surfactant is selected from ($C_{8-18}$ alkyl)(poly)glycosides, ethoxylated $C_8$-$C_{30}$ fatty acid esters of sorbitan, polyethoxylated $C_8$-$C_{30}$ fatty alcohols and polyoxyethylenated $C_8$-$C_{30}$ fatty acid esters, these compounds preferably containing from 2 to 150 mol of ethylene oxide, and mixtures thereof.

Adjuvants

The composition according to the invention may contain one or more adjuvants commonly used in compositions for caring for and/or making up a keratin material, such as water-soluble solvents that may be selected for example, from lower alcohols (mono-alcohols) having from 1 to 6 carbon atoms, such as ethanol; and polyols such as glycerin, glycols such as butylene glycol, isoprene glycol, propylene glycol, polyethylene glycols such as PEG-8; sorbitol; sugars such as glucose, fructose, maltose, lactose, sucrose; and mixtures thereof, to the extent that these compounds do not impair the desired properties of the composition according to the invention. The amount of solvent(s) in the composition of the invention may range for example from 0.1 to 15% by weight, preferably 0.5 to 10% by weight, preferably from 0.5 to 7.5% by weight and more preferably from 0.5 to 5% by weight relative to the total weight of the composition.

Water is not considered here as an adjuvant.

Preservative

The composition may include preservatives. Suitable preservatives include organic acid preservatives may include benzoic acid and alkali metal and ammonium salts thereof (e.g. sodium benzoate), sorbic acid and alkali metal and ammonium salts thereof (e.g. potassium sorbate}, p-Anisic acid and alkali metal, and ammonium salts thereof, and salicylic acid and alkali metal and ammonium salts thereof. Non-limiting examples of preservatives include ethanol, polyvinyl alcohol, phenoxyethanol, benzyl alcohol, salicylic acid, sodium benzoate, caprylyl glycol, methyl paraben, propyl paraben, elhylhexylglycerin, 1,2-propanediol and any mixture thereof.

The pH of the compositions according to the present invention is suitably between 2 and 10, preferably in the range of 4.0 to 8.0, more preferably 4.0 to 7.0 measured at ambient temperature with a suitable pH meter.

The pH of the compositions is for example adjusted with one or more acidic and/or alkaline compounds. An acidic compound can be an inorganic or organic acid or their mixtures. Non-limiting suitable examples are citric acid, lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. Alkaline compounds such as sodium hydroxide can be used to adjust the pH of the compositions.

Various other materials may also be present in the compositions useful in the subject invention. These include humectants, proteins and polypeptides, preservatives and alkaline agents. Examples of such agents are disclosed in the ICI Handbook, pp. 1650-1667.

The inventors have found that a composition according to the present invention allows the preparation of a cleansing product with the desired ideal viscosity.

Viscosity is generally measured at 25° C. after 24 hours, with a rheometer Rheomat 180 with a mobile adapted to the viscosity of the product to be tested (for example spindle M3 and M4), the measure being made after 24 hours rotating the rotor inside the composition, with rotation speed ranging from 5 to 1000 rpm, with shear rate of about 200 $s^{-1}$, and with Torque ranging from 0.25 to 10 mNm, for 10 min.

By "desired ideal viscosity", it is intended to mean that the present invention provide compositions with high viscosity. By "high viscosity" it refers to a composition with a viscosity sufficiently high so the composition does not instantly flow under its own weight at 25° C. and under atmospheric pressure (about 101325 Pa), which also allows for the controlled handling and dispensing of the composition of the present invention during use as compared to a thinner product. An ideal viscosity profile permits the composition of the invention an easy to use product that does not run-off when applied to non-horizontal body surfaces, such as face. More particularly, the desired ideal viscosity of the present invention is from 30 to 90 UD, preferably from 50 to 90 UD using spindle M3 or from 10 to 60 UD, preferably from 10 to 50 UD using spindle M4 (measured in deviation units referred to as UD).

Such composition is generally in the form of a cream or paste. The viscosity of the composition is advantageously adjusted in particular via the ratio (a/b) between a) amino acid surfactant(s) and b) calcium alginate.

The composition according to the invention allows limiting the amount of surfactants in the composition. In one embodiment, the total amount of surfactants is less than 20, or less than 15, or less than 10, by weight percent, based on the total weight of the composition.

Needless to say, a person skilled in the art will take care to select this or these optional additional compound(s), and/or the amount thereof, such that the properties of the composition according to the invention are not, or are not substantially, adversely affected by the envisaged addition.

In one embodiment, the composition of the invention is an aqueous solution.

In one embodiment, the composition of the invention is an emulsion.

Advantageously, the composition of the invention is a cosmetically acceptable composition.

The expression "cosmetically acceptable composition" is understood to mean a non-toxic composition capable of being applied to human keratin materials including the skin, the face, the lips, and the nails.

The composition may be any type of composition for cleansing a keratin material, in particular cleansing composition, and especially for the skin, such as facial cleanser, facial make up remover, body cleanser, or any other types of cleansing composition.

The compositions according to the invention are for example in the form of solutions, gels, milks or creams, more or less flexible, and they can be used on any keratin material such as the skin, scalp, hair, eyelashes, eyebrows, nails or mucous membranes, such as a hygiene product, such as a skin cleanser, mucous membranes and/or hair, especially as a cleansing and/or removing makeup from the skin (the face and/or body), as a shower product (two-in-one), as a shampoo, as a hair conditioner, as a shaving product, as a rinse-off mask, as an exfoliant product (also called peeling or scrub) both for the face, body or hands, after addition of exfoliant particles.

The inventors have found that a composition according to the present invention presents excellent rinse-off speed.

The inventors have found that a composition according to the present invention has a mild skin feeling for a keratin material, especially skin, and more particularly face skin including eyelid, and meanwhile maintaining good cleansing abilities.

The method for evaluating volume of foam is performed for example after applying 0.5 g of a composition according to the invention (or comparative composition) on the face, in the palm, rubbing for 40 rounds by hands in accordance with rotational movements, and collecting all the foam generated, if any (for example by 5 consumers).

The method for evaluating the rinse off speed, cleansing ability, and skin feelings is performed as follows (for example by 5 consumers):

(i) applying 0.5 g of a composition according to the invention (or comparative composition) on the face, and massaging (by rubbing according to round movements) the face with hands for 1 minute;

(ii) cleaning the face with wet hands by rubbing around thereon;

(iii) drying the face with towel;

Rinse off speed is evaluated at step (i) by the number of rounds until tactilely squeaky feeling occurs on the face.

Cleansing ability and skin feeling (for example skin feeling of cleanness, softness, smoothness, mildness, non-dryness, and non-stickiness) are evaluated after step (iii).

The inventors have found that a composition according to the present invention presents a good stability upon storage for 2 months under room temperature (25° C.).

This type of product is appreciated by consumers and renders the product attractive.

The present invention also relates to a use of the composition according to the present invention, as it is or in cosmetic product for cleansing a keratin material, in particular the skin, especially facial skin.

The present invention relates to a method or process for cleansing a keratin material, especially the skin, comprising the application of a composition according to the invention on the keratin material.

In one aspect, the present invention relates to the invention relates to a method or process for cleansing a keratin material, comprising the application, on the surface of said keratin material, of at least one composition of the invention, and optionally rinsing off the composition of the invention, for example with water, to remove the composition from the human keratin material.

The present invention also relates to a non-therapeutic cosmetic process for cleansing human keratin materials comprising applying at least one layer of a composition according to the invention to a keratin material.

The present invention also relates to a method of non-therapeutic cosmetic treatment of human keratinous substances comprising the application of at least one layer of a composition according to the invention to the keratin materials.

The examples that follow are aimed at illustrating the compositions and processes according to this invention, but are not in any way a limitation of the scope of the invention.

All the parts and percentages in the examples are given on a weight basis and all the measurements were obtained at about 25° C., unless otherwise mentioned.

EXAMPLES

Example 1—Invention and Comparative Compositions

| Phase | INCI name | Invention composition (% by weight of the active ingredient) N° composition 1 | 2 | 3 | 4 | Comparative composition (% by weight of the active ingredient) N° composition 1' | 2' |
|---|---|---|---|---|---|---|---|
| A | CALCIUM ALGINATE (Calcium Alginate from Qingdao Bright Moon Seaweed Group Co. Ltd) | 3 | 3 | 3 | 3 | 0 | 0 |
| B | SODIUM LAUROYL SARCOSINATE (30% aqueous solution, ORAMIX L 30 sold by Seppic) | 3 | 0 | 0 | 0 | 0 | 0 |
| B | SODIUM COCOYL GLYCINATE (30% aqueous solution, AMILITE ® GCS-12K sold by Ajinomoto) | 0 | 3 | 0 | 9 | 0 | 9 |
| B | DISODIUM COCOYL GLUTAMATE (and) SODIUM COCOYL GLUTAMATE (25% active ingredients aqueous solution, AMISOFT ® CS-22 sold by Ajinomoto) | 0 | 0 | 3 | 0 | 3 | 0 |
| C | Other polymers ACRYLATES/STEARETH-20 METHACRYLATE COPOLYMER (30% aqueous solution, ACULYN 22 POLYMER, ROHM AND HAAS (DOW CHEMICAL)) | 0 | 0 | 0 | 0 | 3 | 3 |
| D | DECYL GLUCOSIDE (53% aqueous solution, PLANTACARE 2000 UP from Cognis (BASF)) | 0 | 0 | 0 | 5.3 | 0 | 5.3 |
| E | POTASSIUM HYDROXIDE (50% aqueous solution, POTASSIUM HYDROXIDE 50%, CHT SOUTH AFRICA) | 0 | 0 | 0 | 0 | q.s. to pH 6.2 | q.s. to pH 6.2 |
| F | PHENOXYETHANOL (SEPICIDE LD, SEPPIC) | 0.3 | 0.3 | 0.3 | 0.3 | 0.3 | 0.3 |
| F | ETHYLHEXYLGLYCERIN (SENSIVA SC 50, SCHULKE & MAYR) | 0.1 | 0.1 | 0.1 | 0.1 | 0.1 | 0.1 |
| A | WATER | QS 100 | QS 100 | QS 100 | QS 100 | QS 100 | QS 100 |

QS 100: Quantity sufficient to 100% of the total composition weight (for water);
q.s. to pH 6.2: quantity sufficient to reach pH 6.2.

The invention and comparative compositions were prepared using the process conventionally known in the cosmetic field.

Example 2—Evaluation Examples

The viscosity, volume of foam, cleansing ability, rinse off speed, skin feeling after application, and the stability of the invention and comparative formulas were evaluated, according to the above mentioned methods.

The evaluation results are as follow:

| Item | Invention formula 1 | 2 | 3 | 4 | Comparative formula 1' | 2' |
|---|---|---|---|---|---|---|
| Viscosity (spindle type M3 or M4) | 89 (M3) | 35 (M4) | 46 (M4) | 26.5 (M4) | 20 (M3) | 25 (M4) |

| Item | Invention formula 1 | 2 | 3 | 4 | Comparative formula 1' | 2' |
|---|---|---|---|---|---|---|
| Volume of foam | 0 | 0 | 0 | 3 | 1 | 3 |
| Cleansing ability | ok | ok | ok | ok | ok | ok |
| Rinse off speed (number of rounds) | 3 | 3 | 3 | 3 | 6 | 6 |
| Skin feeling (mildness) | 4 | 4 | 4.5 | 4 | 2.5 | 2 |

For the volume of foam the following scores are given:
3: very good;
2: good;
1: poor;
0: no foam generated.

For the skin feeling the following scores are given:
5: excellent;
4: very good;
3: good;
2: poor, tugging feeling after application, dryness;
1: very poor, very dry or heavy and sticky feeling.

Cleansing ability is "ok" if the composition can remove sebum and dirts from skin.

It is observed that the viscosity of the composition according to the invention is better than the viscosity of the comparative composition.

It is observed that the rinse-off speed of the composition according to the invention is better than the rinse-off speed of the comparative composition.

It is observed that skin feeling is improved by the composition according to the invention in view of the comparative composition.

All compositions are stable and present cleansing ability.

The invention claimed is:

1. A composition for cleansing a keratin material, comprising, in an aqueous phase:
a) at least one amino acid surfactant represented by the formula (I):

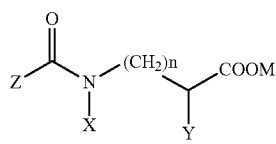

(I)

wherein:
Z represents a saturated or unsaturated, linear or branched hydrocarbon group having 8 to 22 carbon atoms,
X is hydrogen or methyl group,
n is 0 or 1,
Y is selected from the group consisting of hydrogen, $-CH_3$, $-CH(CH_3)_2$, $-CH_2CH(CH_3)_2$, $-CH(CH_3)CH_2CH_3$, $-CH_2C_6H_5$, $-CH_2C_2H_4OH$, $-CH_2OH$, $-CH(OH)CH_3$, $-(CH_2)_4NH_2$, $-(CH_2)_3NHC(NH)NH_2$, $-CH_2C(O)O^-M^+$, $-(CH_2)_2C(O)OH$, and $-(CH_2)_2C(O)O^-M^+$, and
M is a salt-forming cation wherein COO is a counter-anion; and
b) calcium alginate,
wherein a weight ratio (a/b) of a) amino acid surfactant and b) calcium alginate is from 0.7 to 6.

2. The composition of claim 1, wherein a viscosity of the composition is 30 to 90 UD, using spindle M3, or from 10 to 60 UD, using spindle M4.

3. The composition according to claim 1, wherein in formula (I):
n is 0, and
Y is selected from the group consisting of hydrogen, $-(CH_2)_2C(O)OH$, and $-(CH_2)_2C(O)O^-M$.

4. The composition according to claim 1, wherein the amino acid surfactant is at least one selected from the group consisting of sodium lauroyl sarcosinate, sodium cocoyl glycinate, sodium cocoyl glutamate, disodium cocoyl glutamate, and sodium lauroyl glutamate.

5. The composition according to claim 1, wherein an amount of amino acid surfactant ranges from 1 weight percent to 20 weight percent, based on the total weight of the composition.

6. The composition according to claim 1, wherein an amount of calcium alginate ranges from 0.5 weight percent to 10 weight percent, based on the total weight of the composition.

7. The composition according to claim 1, wherein the weight ratio (a/b) of a) and b) is from 0.75 to 5.

8. The composition according to claim 1, further comprising at least one nonionic surfactant.

9. The composition according to claim 8, wherein the nonionic surfactant is at least one selected from the group consisting of ($C_{8-18}$ alkyl)(poly)glycosides, ethoxylated $C_8$-$C_{30}$ fatty acid esters of sorbitan, polyethoxylated $C_8$-$C_{30}$ fatty alcohols and polyoxyethylenated $C_8$-$C_{30}$ fatty acid esters.

10. A composition, comprising:
from 0.5 weight percent to 10 weight percent calcium alginate based on the total weight of the composition;
from 1 weight percent to 20 weight percent amino acid surfactant(s) based on the total weight of the composition; and
water;
wherein a weight ratio (a/b) of a) the amino acid surfactant(s) and b) the calcium alginate is from 0.7 to 6, and
wherein the amino acid surfactant is represented by the formula (I):

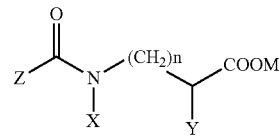

(I)

wherein:
Z represents a saturated or unsaturated, linear or branched hydrocarbon group having 8 to 22 carbon atoms,
X is hydrogen or methyl group,
n is 0 or 1,
Y is selected from the group consisting of hydrogen, $-CH_3$, $-CH(CH_3)_2$, $-CH_2CH(CH_3)_2$, $-CH(CH_3)CH_2CH_3$, $-CH_2C_6H_5$, $-CH_2C_2H_4OH$, $-CH_2OH$, $-CH(OH)CH_3$, $-(CH_2)_4NH_2$, $-(CH_2)_3NHC(NH)NH_2$, $-CH_2C(O)O^-M^+$, $-(CH_2)_2C(O)OH$, and $-(CH_2)_2C(O)O^-M^+$, and
M is a salt-forming cation wherein COO is the counter-anion.

11. The composition according to claim 10, wherein in the formula (I),
n is 0, and
Y is selected from the group consisting of hydrogen, $-(CH_2)_2C(O)OH$, and $-(CH_2)_2C(O)O^-M^+$.

12. A method for cleansing a keratin material, comprising applying a composition according to claim 1 on the keratin material.

13. The composition according to claim 1, comprising:
from 2 weight percent to 10 weight percent of the at least one amino acid surfactant based on the total weight of the composition; and
from 1 weight percent to 6 weight percent calcium alginate based on the total weight of the composition,
wherein the amino acid surfactant is at least one selected from the group consisting of sodium lauroyl sarcosinate, sodium cocoyl glycinate, sodium cocoyl glutamate, disodium cocoyl glutamate, and sodium lauroyl glutamate.

14. The composition according to claim 1, comprising:
from 2 weight percent to 10 weight percent of the at least one amino acid surfactant based on the total weight of the composition; and
from 1 weight percent to 6 weight percent calcium alginate based on the total weight of the composition,
wherein the amino acid surfactant is at least one selected from the group consisting of sodium cocoyl glycinate and disodium cocoyl glutamate.

15. The composition according to claim 1, wherein M is sodium, potassium, ammonium, or triethanolamine.

16. The composition according to claim 10, wherein M is sodium, potassium, ammonium, or triethanolamine.

* * * * *